United States Patent
Dou et al.

(10) Patent No.: US 10,618,889 B2
(45) Date of Patent: Apr. 14, 2020

(54) THIOPHENE MONOAMINE BASED ORGANIC-INORGANIC HYBRID PEROVSKITES

(71) Applicant: Purdue Research Foundation, West Lafayette, IN (US)

(72) Inventors: Letian Dou, West Lafayette, IN (US); Yao Gao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/504,438

(22) Filed: Jul. 8, 2019

(65) Prior Publication Data
US 2020/0062740 A1    Feb. 27, 2020

Related U.S. Application Data

(60) Provisional application No. 62/721,636, filed on Aug. 23, 2018.

(51) Int. Cl.
| | | |
|---|---|---|
| *C07D 409/00* | (2006.01) | |
| *C07D 409/14* | (2006.01) | |
| *C07D 417/14* | (2006.01) | |
| *C07F 7/24* | (2006.01) | |
| *C07D 495/04* | (2006.01) | |
| *C07D 495/14* | (2006.01) | |
| *C07D 513/04* | (2006.01) | |

(52) U.S. Cl.
CPC ......... *C07D 409/14* (2013.01); *C07D 417/14* (2013.01); *C07D 495/04* (2013.01); *C07D 495/14* (2013.01); *C07D 513/04* (2013.01); *C07F 7/24* (2013.01)

(58) Field of Classification Search
CPC .. C07D 409/14; C07D 495/04; C07D 513/04; C07D 417/14; C07D 495/14; C07F 7/24
USPC .......................................................... 549/59
See application file for complete search history.

(56) References Cited

U.S. PATENT DOCUMENTS

| | | |
|---|---|---|
| 6,420,056 B1 | 7/2002 | Chondroudis et al. |
| 2003/0170918 A1 | 9/2003 | Dehaven et al. |
| 2006/0234480 A1 | 10/2006 | Dehaven et al. |

*Primary Examiner* — Taylor V Oh
(74) *Attorney, Agent, or Firm* — Purdue Research Foundation; Zhigang Rao

(57) ABSTRACT

The present disclosure relates to novel thiophene monoamine based organic-inorganic hybrid perovskites, and the method of making and using the novel organic-inorganic hybrid perovskites.

10 Claims, 5 Drawing Sheets

THIOPHENE MONOAMINE BASED ORGANIC-INORGANIC HYBRID PEROVSKITES

CROSS-REFERENCE TO RELATED APPLICATION

This application claims the benefits of U.S. Provisional Application Ser. No. 62/721,636, filed Aug. 23, 2018, the contents of which are incorporated herein entirely.

GOVERNMENT RIGHTS

This invention was made with the United States government support under Department of Energy (DOE) Award No. DE-SC0016356 and National Science Foundation (NSF) Award No. CHE 1625543. The United States government has certain rights in the invention.

TECHNICAL FIELD

The present disclosure relates to novel thiophene monoamine based organic-inorganic hybrid perovskites, and the method of making and using the novel organic-inorganic hybrid perovskites.

BACKGROUND

This section introduces aspects that may help facilitate a better understanding of the disclosure. Accordingly, these statements are to be read in this light and are not to be understood as admissions about what is or is not prior art.

A semiconductor superlattice is commonly made of two materials with different energy band gaps, in which each quantum well sets new selection rules that govern charge carrier distribution, dynamics, and transport. These structures are the foundation of many electronic and optoelectronic devices including light-emitting diodes, lasers, infrared photodetectors, transistors, thermoelectric devices, and solar cells. Conventional semiconductor quantum wells (i.e., mainly group III-V and IV compounds, e.g. GaAs/Al$_x$Ga$_{1-x}$As/GaAs) are grown in a layer-by-layer fashion under high temperature and high vacuum conditions. Their properties and performance are limited by interfacial lattice mismatch. Thus, the fabrication of defect-free quantum wells using new materials via innovative and cost-effective methods has been of great interest for a long time.

Two-dimensional (2D) semiconductor superlattices (or quantum wells), which are usually fabricated through metal-organic chemical vapor deposition or molecular beam epitaxy, are key building blocks in modern optoelectronics. The ability to simultaneously realize defect-free epitaxial growth and to individually fine-tune the chemical composition, layer thickness, and band structure of each layer is essential for achieving the desired device performance. Such structures are challenging to realize using organic or hybrid materials.

Organic semiconductors offer great structure and property tunability through synthetic manipulation of their molecular motifs. Moreover, their weak inter-molecular van der Waals interactions make them much more tolerant towards lattice mismatch. Quantum wells based on organic materials were initially investigated in the 1990s. See U.S. Pat. No. 6,420,056. However, key challenges remain to growing organic superlattices, including controlling the crystallinity and layer uniformity at the nanometer scale and reducing interdiffusion at the organic-organic interface.

Two-dimensional (2D) layered halide perovskites have also attracted considerable attention. See U.S. Pat. No. 6,420,056. 2D perovskite structures can be understood as atomically thin slabs cut from the 3D parent structures along different crystal directions that are sandwiched by two layers of large organic cations. While there is a large number of reports regarding 2D perovskites that incorporate insulating aliphatic ammonium cations, only few efforts have been made to incorporate electronically-active organic moieties. However, in most attempts only polycrystalline thin films with low crystallinity were obtained. Common to all reports was that the incorporating of large conjugated organic groups into the inorganic matrix to make high quality superlattices was found to be challenging. To date, a fundamental understanding about how molecular structure influence the overall morphology and properties of the perovskites is still lacking, and the range of organic cations that can be incorporated into the lattice remains limited.

High-quality organic-inorganic hybrid perovskite quantum wells with tunable structures and band alignments are therefore still needed.

SUMMARY

The present disclosure relates to novel thiophene monoamine based organic-inorganic hybrid perovskites, and the method of making and using the novel organic-inorganic hybrid perovskites.

In one embodiment, the present disclosure provides an organic-inorganic hybrid perovskite of Formula I:

$$(R^1NH_3^+)_2(A^+)_{n-1}(M^{2+})_n(X^-)_{3n+1}$$

wherein:
($R^1NH_3^+$) represents:

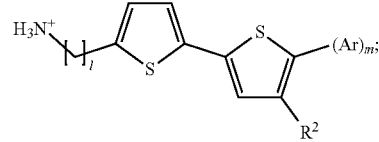

$A^+$ represents a cation Cs$^+$, Rb$^+$, CH$_3$NH$_3^+$, CH$_3$CH$_2$NH$_3^+$, or

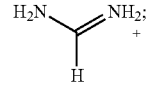

$R^2$ is —H, —F, —Cl, —Br, —I, -Me, -Et, —OMe, —OEt, —SMe, —SEt, —CN, —NO$_2$, —COMe, —CHO, —COOMe, or —NH—COMe;

(Ar)$_m$ represents a conjugated and optionally substituted aryl or hetero aryl system, or a combination thereof, wherein each aryl or hetero aryl ring in the conjugated and optionally substituted aryl or hetero aryl system may be same or different;

$M^{2+}$ represents a divalent metal cation Pb$^{2+}$, Sn$^{2+}$, Ge$^{2+}$, Cu$^{2+}$, Zn$^{2+}$, Cd$^{2+}$, Hg$^{2+}$, Ni$^{2+}$, Co$^{2+}$, Fe$^{2+}$, Mn$^{2+}$, Cr$^{2+}$, V$^{2+}$, Pd$^{2+}$, Pt$^{2+}$, or a combination thereof; or a combination of one monovalent metal cation selected from the group consisting of Ag$^+$, Cu$^+$, Tl$^+$, Au$^+$, and one trivalent metal cation selected from the group consisting of Bi$^{3+}$, Sb$^{3+}$, In$^{3+}$, As$^{3+}$, Au$^{3+}$, Y$^{3+}$, to make the average valence of the metal cation to be 2+;

X is F, Cl, Br or I;
l is 1-4;
m is 0-5; and
n is 1-6;
wherein the positions of $R^2$ and $(Ar)_m$ on the thiophenyl ring can be exchanged.

DETAILED DESCRIPTION

Figure 1:
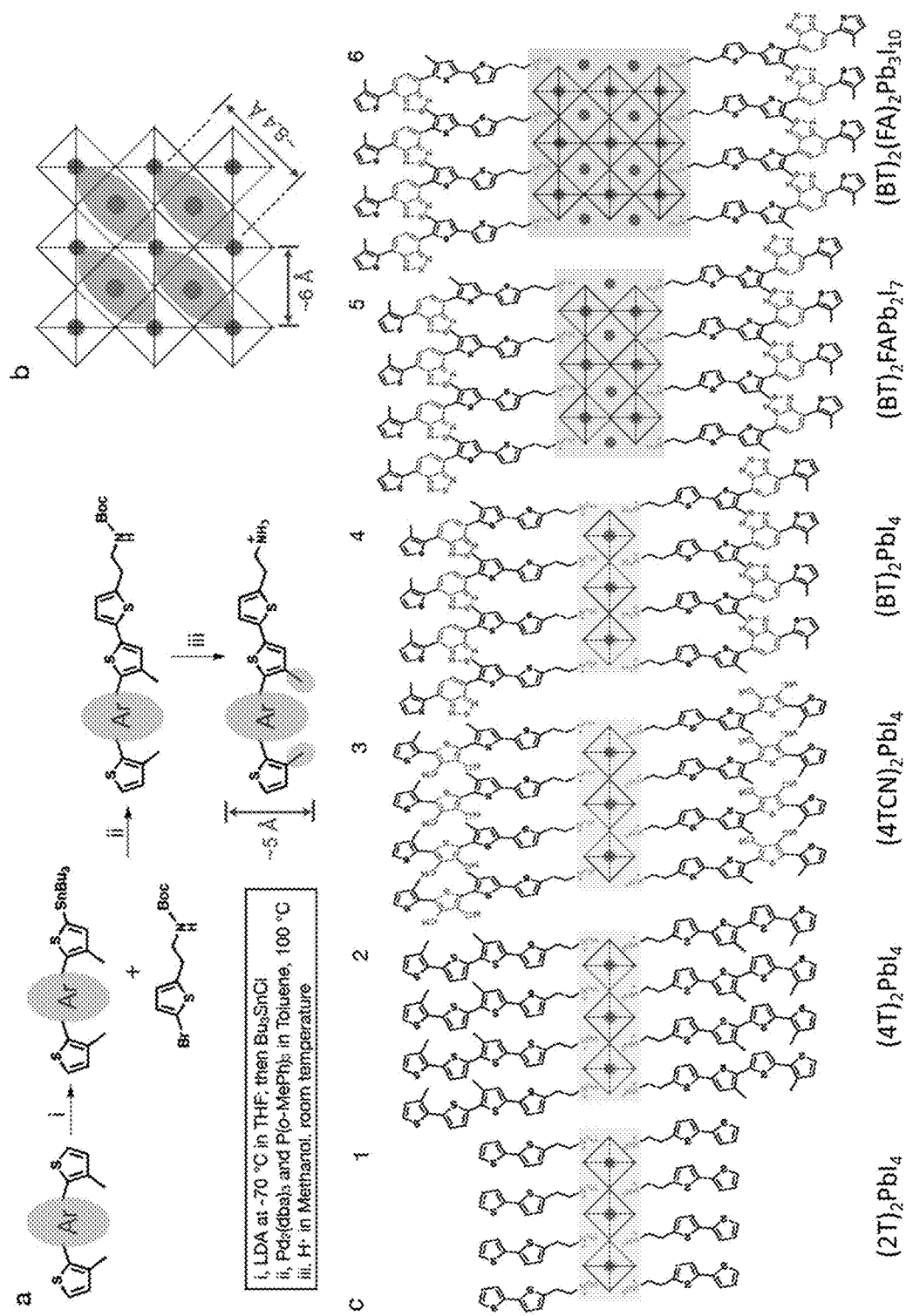
FIG. 1 shows synthetic route to hybrid 2D perovskite quantum wells. a) Proposed molecular design and synthetic route for the conjugated organic ligands. The purple oval represents different conjugated building blocks. b) Top view of an ideal cubic phase halide perovskite (001) crystal plane. The blue dots indicate B site atom (e.g. $Pb^{2+}$); the red ellipse represents the position of the organic cations. c) Proposed idealized crystal structures of the organic-inorganic hybrid 2D perovskites (side view).

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N (R)C(O)OR, (CH$_2$)$_{0-2}$N(R)N(R)$_2$, N(R)N(R)C(O)R, N(R)N (R)C(O)OR, N(R)N(R)CON(R)$_2$, N(R)SO$_2$R, N(R)SO$_2$N (R)$_2$, N(R)C(O)OR, N(R)C(O)R, N(R)C(S)R, N(R)C(O)N (R)$_2$, N(R)C(S)N(R)$_2$, N(COR)COR, N(OR)R, C(=NH)N (R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A "hetero aryl" represents aromatic ring comprising at least one hetero atom such as N, S, O, or Se. Hetero aryl in the present disclosure may be any hetero aryl. Hetero aryl in the present disclosure may be but is not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, benzimidazolinyl groups, or any combination thereof.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

In one embodiment, the present disclosure provides an organic-inorganic hybrid perovskite of Formula I:

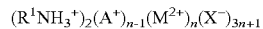

wherein:
($R^1NH_3^+$) represents:

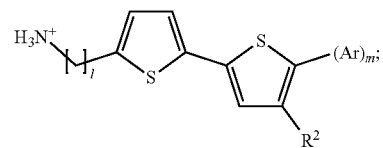

$A^+$ represents a cation $Cs^+$, $Rb^+$, $CH_3NH_3^+$, $CH_3CH_2NH_3$, or

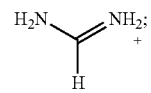

$R^2$ is —H, —F, —Cl, —Br, —I, -Me, -Et, —OMe, —OEt, —SMe, —SEt, —CN, —$NO_2$, —COMe, —CHO, —COOMe, or —NH—COMe;

$(Ar)_m$ represents a conjugated and optionally substituted aryl or hetero aryl system, or a combination thereof, wherein each aryl or hetero aryl ring in the conjugated and optionally substituted aryl or hetero aryl system may be same or different;

$M^{2+}$ represents a divalent metal cation $Pb^{2+}$, $Sn^{2+}$, $Ge^{2+}$, $Cu^{2+}$, $Zn^{2+}$, $Cd^{2+}$, $Hg^{2+}$, $Ni^{2+}$, $Co^{2+}$, $Fe^{2+}$, $Mn^{2+}$, $Cr^{2+}$, $V^{2+}$, $Pd^{2+}$, $Pt^{2+}$, or a combination thereof; or a combination of one monovalent metal cation selected from the group consisting of $Ag^+$, $Cu^+$, $Tl^+$, $Au^+$, and one trivalent metal cation selected from the group consisting of $Bi^{3+}$, $Sb^{3+}$, $In^{3+}$, $As^{3+}$, $Au^3$, $Y^{3+}$, to make the average valence of the metal cation to be 2+;

X is F, Cl, Br or I;
l is 1-4;
m is 0-5; and
n is 1-6;
wherein the positions of $R^2$ and $(Ar)_m$ on the thiophenyl ring can be exchanged.

In one embodiment, the present disclosure provides an organic-inorganic hybrid perovskite of Formula I, wherein $A^+$ is a cation selected from $CH_3NH_3^+$, $CH_3CH_2NH_3^+$, or

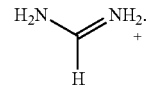

In one embodiment, the present disclosure provides an organic-inorganic hybrid perovskite of Formula I, wherein $R^2$ is —F, —Cl, —Br, —I, -Me, -Et, —OMe, —OEt, —SMe, —SEt, —CN, —$NO_2$, —COMe, —CHO, —COOMe, or —NH—COMe. In one aspect, $R^2$ is -Me.

In one embodiment, the present disclosure provides an organic-inorganic hybrid perovskite of Formula I, wherein $(Ar)_m$ represents a conjugated and optionally substituted aryl or hetero aryl system, or a combination thereof, wherein each aryl or hetero aryl ring in the conjugated and optionally substituted aryl or hetero aryl system may be same or different, wherein aryl is phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, naphthyl, or any combination thereof; wherein hetero aryl is pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

In one embodiment, the present disclosure provides an organic-inorganic hybrid perovskite of Formula I, wherein (Ar)$_m$ represents a conjugated and optionally substituted aryl or hetero aryl system, or a combination thereof, wherein each aryl or hetero aryl ring in the conjugated and optionally substituted aryl or hetero aryl system may be same or different, wherein Ar is:

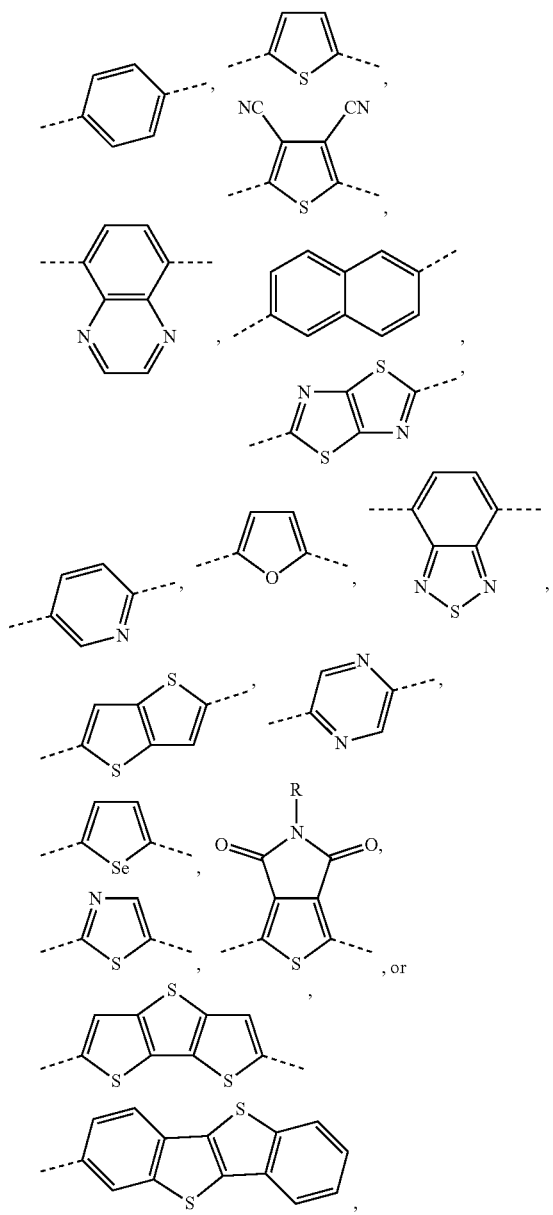

or any combination thereof. The dashed bonds shows possible connection between different aryl groups. It should be understood that the bond positions may not be limited to the as-drawn structures. In one aspect, one or more aryl group may be substituted by substituent groups such as —F, —Cl, —Br, —I, -Me, -Et, —OMe, —OEt, —SMe, —SEt, —CN, —NO$_2$, —COMe, —CHO, —COOMe, —NH—COMe, or any combination thereof.

In one embodiment, the present disclosure provides an organic-inorganic hybrid perovskite of Formula I, wherein M$^{2+}$ is a divalent metal cation Pb$^{2+}$, Sn$^{2+}$, Ge$^{2+}$, Cu$^{2+}$, Zn$^{2+}$, Cd$^{2+}$, Hg$^{2+}$, Ni$^{2+}$, Co$^{2+}$, Fe$^{2+}$, Mn$^{2+}$, Cr$^{2+}$, V$^{2+}$, Pd$^{2+}$, Pt$^{2+}$ or any combination thereof.

In any embodiment, the present disclosure provides an organic-inorganic hybrid perovskite of Formula I, wherein there is only one ammonium (NH$_3^+$) group in Formula I to ensure thiophene monoamine based organic-inorganic hybrid perovskites.

In any embodiment, the present disclosure provides an organic-inorganic hybrid perovskite of Formula I, wherein R$^1$NH$_3^+$ represents asymmetric mono-ammonium cationic moiety.

In one embodiment, the present disclosure provides an organic-inorganic hybrid perovskite of Formula I, wherein R$^1$NH$_3^+$ is:

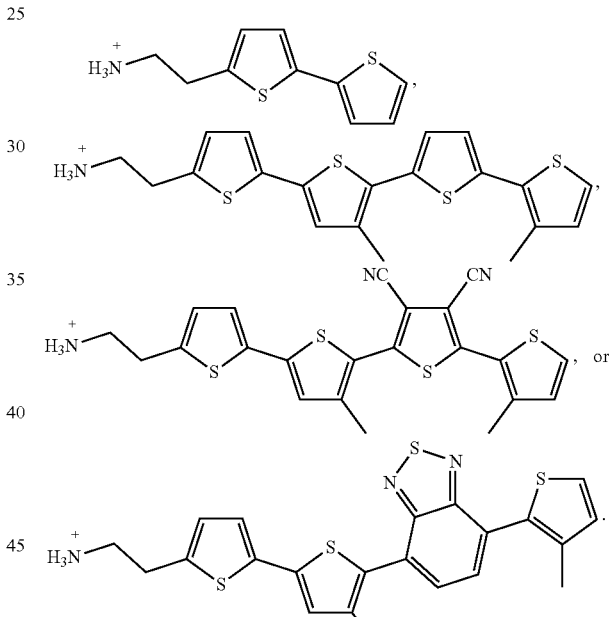

The present disclosure provided a molecular-design approach to synthesize a variety of structurally-tunable organic-inorganic hybrid perovskite quantum wells in both nanocrystal and bulk forms and present a systematic investigation on their unique structural, spectroscopic, and electronic properties. FIG. 1a shows the general synthetic route towards the new π-conjugated organic cations. A tert-butyloxycarbonyl (Boc) protected amine group can be incorporated into the target molecules via a Pd-catalyzed cross-coupling reaction (step ii in FIG. 1a). In the subsequent step, the Boc group can be easily cleaved using simple Brønsted acids. If hydrogen halide species (i.e., HCl, HBr, or HI) are used as the catalyst they also serve as a halide source to create the unprotected ammonium halide species. The present disclosure chose asymmetric mono-ammonium cationic species over symmetric bis-ammonium cations to achieve absolute control over the surface chemistry (i.e. to ensure that the surface is terminated by an organic group). In this paradigm, two important molecular design criteria needed to be taken into consideration. First, steric demand restricts the range of cations that can be matched with the perovskite lattice. FIG. 1b illustrates the (001) plane of an ideal cubic phase lead-iodide perovskite crystal lattice. Each $Pb^{2+}$ atom is surrounded by six $I^-$ atoms forming an octahedron, and each octahedron shares four corners to form an infinite sheet. The ammonium groups of the large organic cations locate in the vacancies between these octahedrons and align the organic fragments perpendicularly to the (001) plane. Due to the spatial constraints, the maximum width of the organic molecule has to be ~8.4 Å or less. Second, it is found that there is a strong tendency for the organic cations to self-aggregate due to π-π interactions, and these strong interactions can easily lead to phase separation of the organic and inorganic components. To address this issue, it was surprisingly found that small substituents on the cations can modulate intermolecular interactions and help prevent self-aggregation/crystallization. Considering both the steric hindrance and self-aggregation effects, it was decided to incorporate two methyl groups in the molecular design (highlighted in green in FIG. 1a).

Figure 2:
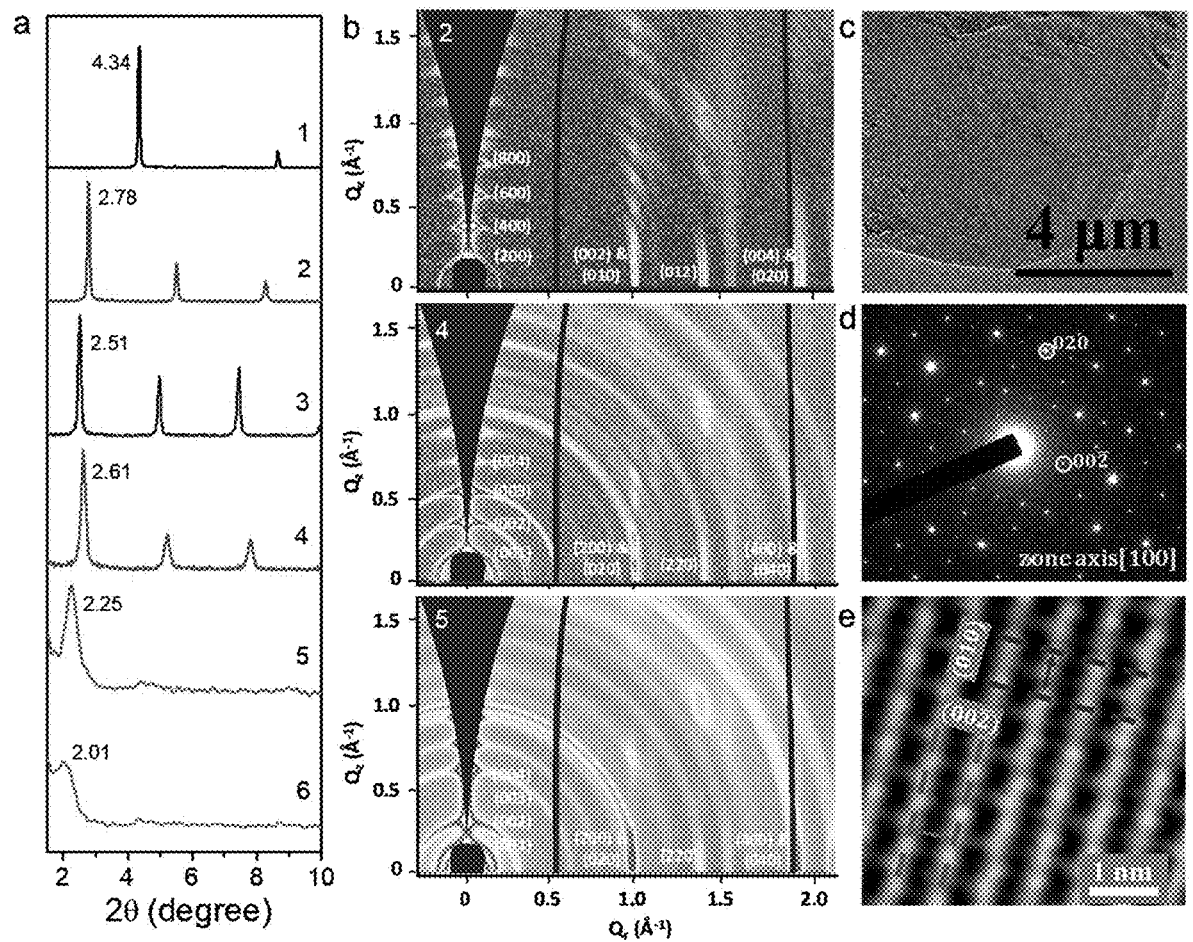
FIG. 2 shows thin film and crystal structure characterization of layered hybrid perovskites. a) Out-of-plane XRD patterns of polycrystalline thin films of $(2T)_2PbI_4$ (compound 1), $(4T)_2PbI_4$ (compound 2), $(4TCN)_2PbI_4$ (compound 3), $(BT)_2PbI_4$ (compound 4), $(BT)_2(FA)Pb_2I_7$ (compound 5), and $(BT)_2(FA)_2Pb_3I_{10}$ (compound 6). b) GIWAXS patterns for perovskite films with Miller indices of prominent peaks marked. The color scale is proportional to the intensity of X-ray scattering. c) TEM image of the $(4T)_2PbI_4$ thin sheet. d) Electron diffraction pattern of the nanocrystal sheet of $(4T)_2PbI_4$. e) Amplification result of low dose filtered HRTEM image of $(4T)_2PbI_4$ nanocrystal sheet.

Based on this design strategy, the present disclosure provided synthesis for a series of conjugated organic cations featuring an electron-rich thiophene unit and electron-deficient 3,4-dicyanothiophene or 2,1,3-benzothiadiazole units (for short, the molecules are abbreviated as 4T, 4TCN, and BT, respectively). For comparison, the present disclosure provided synthesis for a short conjugated organic ligand containing a bisthiophene unit (2T). FIG. 1c shows the corresponding molecular structures and the illustration of the 2D hybrid perovskite structures. The present disclosure presented six hybrid perovskites quantum wells by systematically tuning the structure of the organic and inorganic layers: $(2T)_2PbI_4$ (compound 1), $(4T)_2PbI_4$ (compound 2), $(4TCN)_2PbI_4$ (compound 3), $(BT)_2PbI_4$ (compound 4), $(BT)_2(FA)Pb_2I_7$ (compound 5), and $(BT)_2(FA)_2Pb_3I_{10}$ (compound 6), where FA is formamidinium cation. In initial experiments, thin film samples were prepared by spin-coating and confirmed the phase purity of each structure using out-of-plane X-ray diffraction (XRD) (FIG. 2a). The interlayer d-spacing distances were calculated to be 20.3 Å, 31.8 Å, 35.2 Å, 33.8 Å, 39.2 Å and 43.9 Å for compounds 1-6, respectively. Although 4T and 4TCN are almost identical in length, the interlayer distances of compound 2 and 3 are different, indicating that the inclination of the cations with respect to the perovskite layers must be different in these materials. The samples were further characterized using grazing incidence wide angle X-ray scattering (GI-WAXS). All samples show strong periodic peaks along the $Q_z$ direction, in good agreement with the out-of-plane XRD results. The 2D images also reveal the orientation distribution with respect to the substrates, assuming isotropy in the in-plane directions. For thin films 1-3, a strong preference for orientation along the substrate normal with a small isotropic background was observed. In contrast, thin films 4-6 show a broader distribution, indicating the existence of both out-of-plane and in-plane orientations. All samples share a number of other peaks. For example, diffractions peaks at $Q_{x-y}$~1.45 $Å^{-1}$ are common for all samples, indicating they have similar in-plane lattice constants.

To better elucidate the structural properties of these new 2D hybrid perovskites, the present disclosure attempted to determine their structures by single crystal X-ray diffraction. For $(4T)_2PbI_4$ and $(BT)_2PbI_4$ orange and red plate crystals of sufficiently high quality could be obtained. The inorganic layers and part of the organic layers of the two structures are quite similar, as can be seen in an overlay of the two crystal structures; distinct differences start to appear at the position of the benzothiadiazole unit of the BT ligand. The basic structure of these two compounds is in both cases monoclinic C-centered and the structures are close to be being isotypic. However, in $(BT)_2PbI_4$ the monoclinic symmetry is broken, and instead a triclinic superstructure is formed (see FIG. S6 and related discussion for details). Note, in both structures the environment of the lead atoms is substantially distorted from ideal octahedral. The lead ion is displaced from the central position of the octahedron towards one of the apical iodine, and away from the other, leading to apical Pb—I bond distances of 3.022(7) and 3.464(7) Å in $(4T)_2PbI_4$ (the equatorial Pb—I bonds are 3.137(2) Å). In $(BT)_2PbI_4$, the equivalent shortest and longest apical Pb—I bond distances are 2.996(5) and 3.438(4) Å. This non-centrosymmetric feature suggests possible ferroelectricity in these materials.

In addition to polycrystalline thin films and single crystals, the present disclosure also applied substrate-guided solvent evaporation method to prepare ultrathin 2D crystals. FIG. 2c displays a low magnification transmission electron microscopy (TEM) image of the atomically thin $(4T)_2PbI_4$ crystal. FIGS. 2d and 2e show the corresponding results of selected area electron diffraction (SAED) and low-dose filtered high-resolution TEM. The present disclosure were able to observe the lattice fringes of the 2D sheet. The diffraction data also match well with the other XRD and GIWAXS data. Both SAED and HRTEM results indicate the single crystalline feature of the nanocrystals. All these studies reveal the layered perovskite quantum well structure of hybrid materials provided in the present disclosure.

Figure 3:
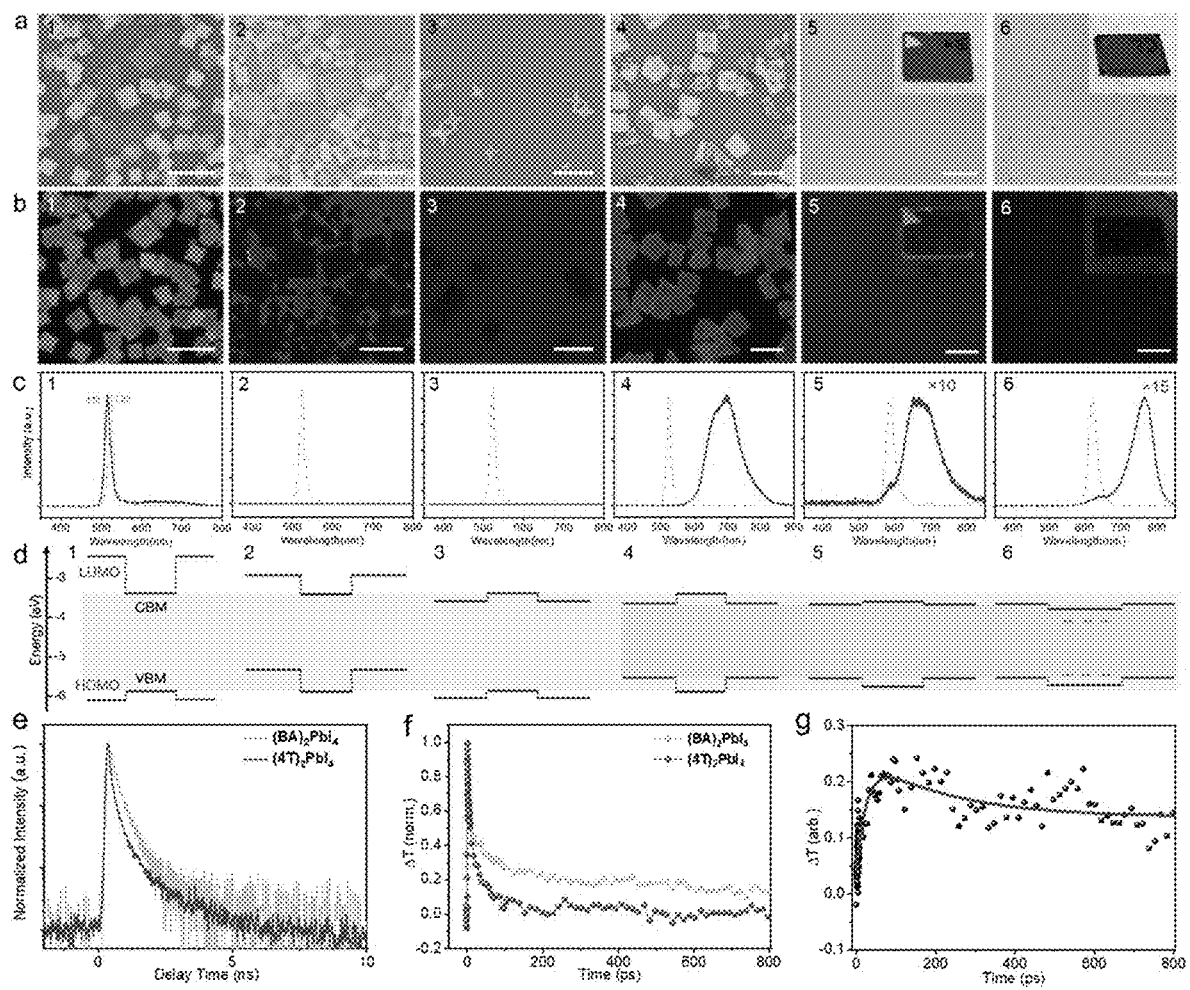
FIG. 3 shows optical properties band alignments of the 2D hybrid halide perovskites. a) Optical microscopy images of the 2D crystals grown on $SiO_2/Si$ substrates: $(2T)_2PbI_4$ (compound 1), $(4T)_2PbI_4$ (compound 2), $(4TCN)_2PbI_4$ (compound 3), $(BT)_2PbI_4$ (compound 4), and thin films spin coated on glass substrates: $(BT)_2(FA)Pb_2I_7$(compound 5) and $(BT)_2(FA)_2Pb_3I_{10}$ (compound 6). b) Corresponding PL image of the 2D crystals and thin films under UV (wavelength ~380 nm) excitation. All scale bars are 10 μm for 1-6. c) Corresponding steady state PL spectra of the 2D crystals and thin films (red curves) compared with PL spectra of BA based counterparts (light grey dashed curves). The PL is quenched for crystal 2 and 3, indicating a type II band alignment and efficient charge separation at the organic-inorganic interface. d) Semi-quantified band structures of the hybrid 2D perovskite superlattices. The black lines indicate the conduction band minimum (CBM) and valence band maximum (VBM) of the perovskite part; the red lines indicate the highest occupied molecular orbital (HOMO) and lowest unoccupied molecular orbital (LUMO) of the organic part. e) Time-resolved PL spectra of $(4T)_2PbI_4$ (compound 2) 2D crystal (red curve) compared with BA based counterparts (grey curve). f) Bleach dynamics of $(BA)_2Pb_4$ crystal (grey curve) and $(4T)_2PbI_4$ crystal (red curve). g) Extraction of the hole transfer time in $(4T)_2PbI_4$, by subtracting the bleach dynamics of the $(BA)_2PbI_4$ crystal from those of $(4T)_2PbI_4$ crystal. The resulting curve is fit with an exponential growth of 26±7 ps.

The present disclosure characterized the optical properties and charge carrier dynamics of the quantum well structures using steady-state and time-resolved spectroscopy. FIG. 3a shows optical microscope images of the ultrathin 2D crystals (for compounds 1 to 4) and of thin films of compounds 5 and 6. 2D sheets with lateral size of around 10 to 20 μm and well-defined square shapes were obtained. For compound 3, the shape of the crystal differs from the square plate appearance of the other compounds, having instead a four-fold star-shaped symmetry. A possible cause could be the twinning effect. The surface morphology of these 2D crystals and corresponding thin films were also investigated by atomic force microscopy. Ultrathin 2D crystals (10 to 100 nm thick) with similar shapes have been observed.

FIG. 3b shows the corresponding photoluminescence (PL) images under UV irradiation (wavelength ~380 nm). Compound 1 exhibits a green color, compounds 2 and 3 display no PL, while compound 4 shows a red color. The thin film of compound 5 has a faded red PL and compound 6's PL is quenched (FIG. 3c, the red curves). For comparison, the PL spectrum of the previously reported 2D perovskite $(BA)_2PbI_4$ (BA=butyl ammonium) is also shown (the grey dashed curves). Crystals of compound 1 show a strong and narrow green PL with a peak at 515 nm (full width at half maximum is 20 nm), which is very close to that of their BA based counterpart, indicating that the PL originates from the inorganic layer; compound 4 shows a strong red PL at ~700 nm, which is from the conjugated organic ligands, while no PL from the inorganic layer is detected. These results indicate that energy resonates and transfers efficiently to the lowest energy emitter. For compound 2 and 3, emissions from both the inorganic layer and the organic layers are completely quenched, suggesting efficient charge separation (exciton dissociation) occurs at the organic-inorganic interface. For compound 5, the intensities of red PL become much weaker than for compound 4. In compound 6, the PL from the organic group is quenched, and PL at a longer wavelength is detected, which is probably from a phase impurity of the thin film (e.g. a higher n number or a 3D perovskites). Absorption spectra of these perovskite thin films and pure organic conjugated ligands are also consistent with the PL results.

To better clarify their band alignments, ultraviolet photoelectron spectroscopy (UPS) and cyclic voltammetry (CV) were employed to characterize the valence band maximums (VBM) of the inorganic perovskite layers and the highest occupied molecular orbital (HOMO) energy levels of the conjugated organic ligands. The VBM of the n=1, n=2 and n=3 2D perovskite thin films are −5.89 eV, −5.83 eV and −5.79 eV, respectively. The HOMO energy levels of 4T, 4TCN and BT were further deduced to be ~5.28 eV, −6.07 eV and −5.58 eV, respectively. The HOMO energy level of 4T was cross-checked using both UPS and CV methods. Given the VBM and HOMO energy levels, the conduction band minimum (CBM) and the lowest unoccupied molecular orbital (LUMO) energy levels can be calculated along with their optical bandgaps. The present disclosure depicted the semi-quantitative band alignments for these hybrid 2D crystals to be type I, type II, type II (reverse), type I (reverse), type I (reverse) and type II for compound 1-6 (FIG. 3d), respectively. Density functional theory calculations were performed to calculate the VBM/CBM of the perovskites and the HOMO/LUMO energies of the organic ligands. The relative positions predicted agree with the experimental trends discussed above.

Next, the present disclosure employed transient absorption (TA) spectroscopy to investigate the charge transfer processes in $(4T)_2PbI_4$. The decrease in PL lifetime (FIG. 3e), as well as the significant quenching (~1,000-fold) of the PL intensity is consistent with a type II heterojunction being formed at the interface between 4T and the $Pb_4$ layer. Exciton dissociation could occur at this interface by electrons transferring from 4T molecules to the $Pb_4$ layer and holes transferring from $Pb_4$ units to 4T molecules. To elucidate the hole transfer time, we compared the exciton bleach dynamics in $(4T)_2PbI_4$ to those in $(BA)_2PbI_4$ where no exciton dissociation is expected (FIG. 3f-3g). Exciton dynamics probed at 515 nm decayed more rapidly in $(4T)_2PbI_4$ than in $(BA)_2PbI_4$, consistent with hole transfer. The present disclosure extracted the hole transfer time, by subtracting the dynamics in $(BA)_2PbI_4$ from those in $(4T)_2PbI_4$, and the hole transfer time was determined to be 26±7 ps. The ultrafast charge transfer process is likely facilitated by the short distance between the inorganic and the organic layers. It was found that the distance from the tip of the $PbI_4^{2-}$ octahedron to the first thiophene unit is only 4.07 Å, which is similar to that of a normal π-π stacking distance.

Figure 4:
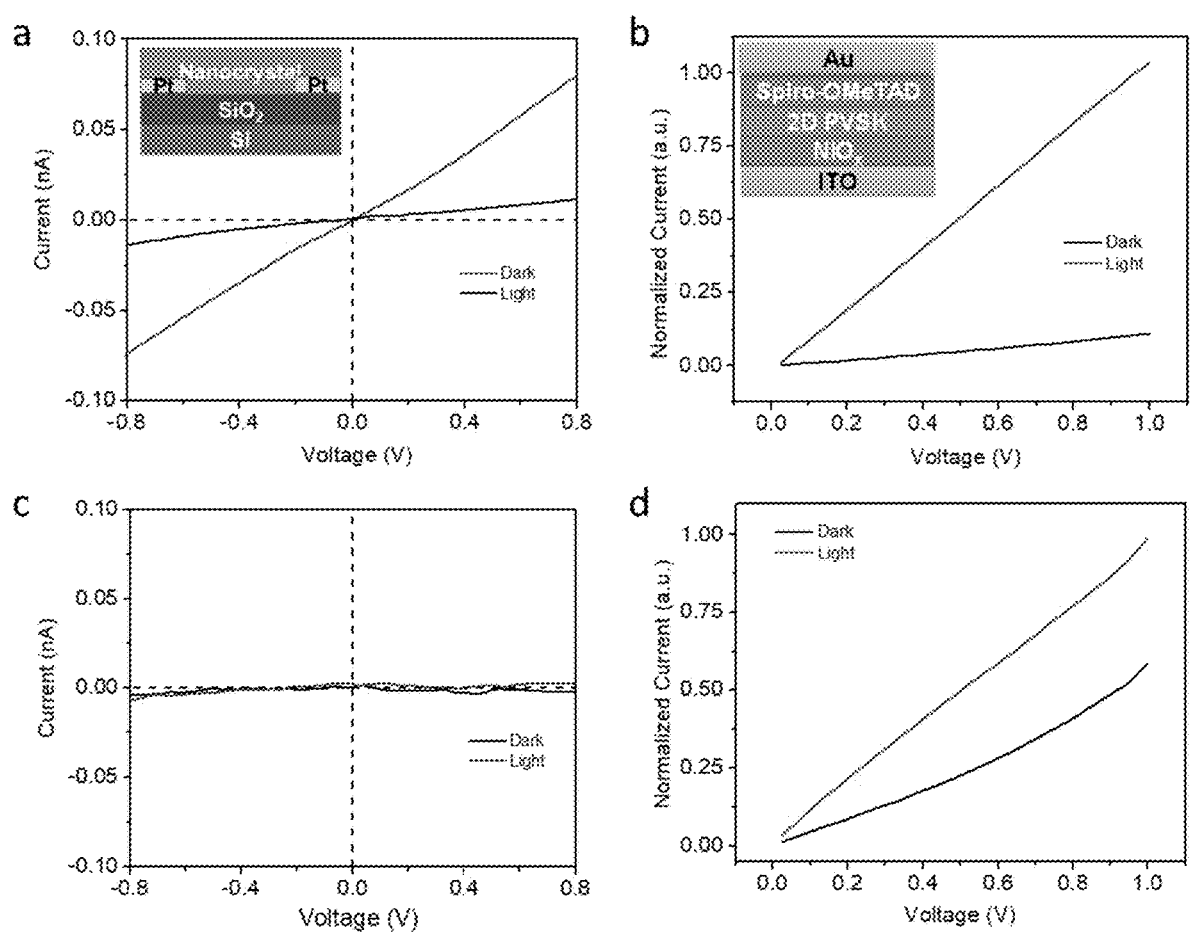
FIG. 4 shows characterization of two terminal lateral and vertical devices. a) I-V characteristics of a $(4T)_2PbI_4$ nanocrystal. The device structure is shown in the inset. b) I-V characteristics of $(4T)_2PbI_4$ thin film-based device, and the device structure is shown in the inset. c) and d), the corresponding electrical characterization of a $(BA)_2Pb_4$ nanocrystal and thin film for comparison.

The present disclosure further quantified the effects of the structural and compositional variations on their fundamental electrical properties. $(BA)_2PbI_4$ with insulating organic ligands and $(4T)_2PbI_4$ with semiconducting ligands (type II junction) were chosen as the model systems and their conductivity in both vertical and lateral directions were compared. 2D crystals were directly grown on the pre-patterned electrodes to test their lateral conductivity, while the vertical conductivity experiments were carried out on the thin film devices. For both the lateral (FIG. 4a) and the vertical (FIG. 4b) devices, $(4T)_2Pb_4$ exhibited a small conductivity in the dark (indicating a very low intrinsic carrier concentration). The conductivity of the devices under light irradiation were ~8 times enhanced for the lateral device and ~100 times enhanced for the vertical device. In contrast, the differences between the dark and light currents for $(BA)_2PbI_4$ were much smaller (FIGS. 4c and 4d). No obvious change was found in lateral devices and a ~2-fold enhancement was found for the vertical devices. The considerable conductivity enhancement under photoexcitation in $(4T)_2PbI_4$ is consistent with it being a type II quantum well structure with an increased charge carrier concentration. The ultrafast photo-induced charge separation and the substantially enhanced photoconductivity in the type II organic-perovskite heterojunctions suggest these compounds to be promising for applications in high gain photodetectors and efficient photovoltaics.

Figure 5:
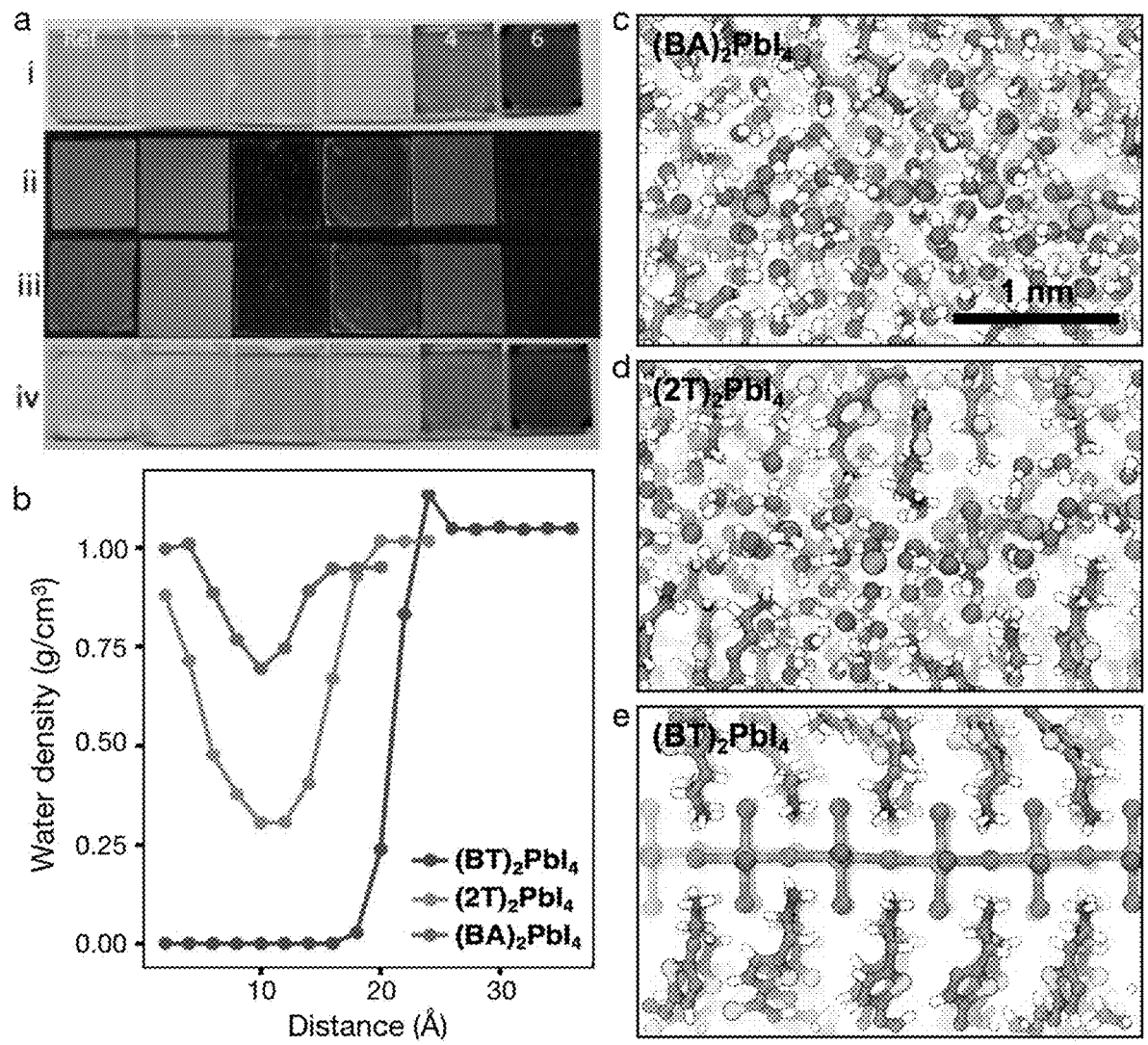
FIG. 5l shows Stability of 2D hybrid halide perovskite thin films and the possible mechanism. a) Photos of 2D hybrid halide perovskite thin films with different organic ligands under natural light (i, iv) and UV lamp irradiation (ii, iii) before (i, ii) and after immersion in water (iii, iv). b) Water density profiles averaged over the last 1 ns of the dynamics. The origin is set by the original perovskite surface and errors are within the marker size. c-e) Snapshots from the molecular dynamics simulations for $(BA)_2PbI_4$ (top), $(2T)_2PbI_4$ (middle), and $(BT)_2PbI_4$ (bottom), showing a 2 nm cross-section of each perovskite layer after 1 ns of equilibration.

A major challenge for perovskite optoelectronics is their poor chemical and thermal stability. Here, The present disclosure demonstrated the outstanding stability of the new 2D hybrid halide perovskites by immersing them in deionized water without any protective layer. FIG. 5a shows photographs comparing the samples under white light and UV light illumination before and after immersion in water. The $(BA)_2PbI_4$ thin films degrade and their PL disappears immediately when coming into contact with water (despite the fact that $(BA)_2PbI_4$ is known to be more resilient to moisture/water than 3D perovskites). The green PL of $(2T)_2PbI_4$ (compound 1) thin film was retained for about one minute and then started to degrade. Surprisingly, other perovskite thin films with larger conjugated ligands exhibit excellent stability over prolonged periods. The XRD patterns of these thin films show no change after 5 minutes in water. $(4T)_2PbI_4$ (compound 2) and $(BT)_2PbI_4$ (compound 4) perovskite thin films are indeed stable towards water for periods as long as a week, and they also exhibit excellent thermal stability, showing no signs of decomposition up to 250° C.

The origin of this enhanced stability was investigated using molecular dynamics simulations of $(BA)_2PbI_4$, $(2T)_2PbI_4$, and $(BT)_2PbI_4$ with direct immersion in water. In the simulations, the films were initially dehydrated and allowed to equilibrate with bulk water over 2 ns. FIG. 5b summarizes the quantitative distribution of water molecules around the perovskites. It was found that water penetrates the $(BA)_2PbI_4$ organic layer and completely dissolves the surface cations within 2 ns (FIG. 5c). In the water density profile (FIG. 5b), cation dissolution is evident in the reduction in water density for intermediate separations of 5-15 Å. The intermediate case of $(2T)_2PbI_4$ exhibits partial penetration of water into the organic layer via dissolution of some surface cations and the formation of well-defined channels (FIG. 5d). Interestingly, the $(BT)_2PbI_4$ film exhibits minimal water penetration into the upper organic layer and the inorganic surface remains dehydrated (FIG. 5e). Based on these simulations, it was concluded that water penetration accompanied by cation dissolution may be the primary mechanism of decomposition. The bulky and hydrophobic organic conjugated groups were able to effectively protect the halide perovskites and dramatically enhance their environmental stability, making these materials more suitable for practical uses.

The present disclosure demonstrated that the organic and inorganic building blocks of hybrid perovskite materials can be manipulated in a modular fashion to produce tunable Type 1 and Type 2 heterojunctions. The materials' design and synthesis strategy presented here could serve as a blueprint for many other functional complex organic molecules. The overall optical and electronic properties are determined by the interaction of these two components. These atomically thin 2D building blocks can be easily assembled to form ultrathin crystals or macroscopic functional films. This work may open up an avenue towards molecularly engineered solution-processed semiconductors quantum wells with strikingly high intrinsic stability for potential applications in electronics, optoelectronics, and photonics.

Materials Synthesis

All reactions sensitive to air and water were performed in an inert (argon) atmosphere using a Schlenk line setup and tubes. All chemical reagents and solvents were purchased from Sigma-Aldrich and used as received.

Scheme 1: Synthesis of the Organotin Reagents:

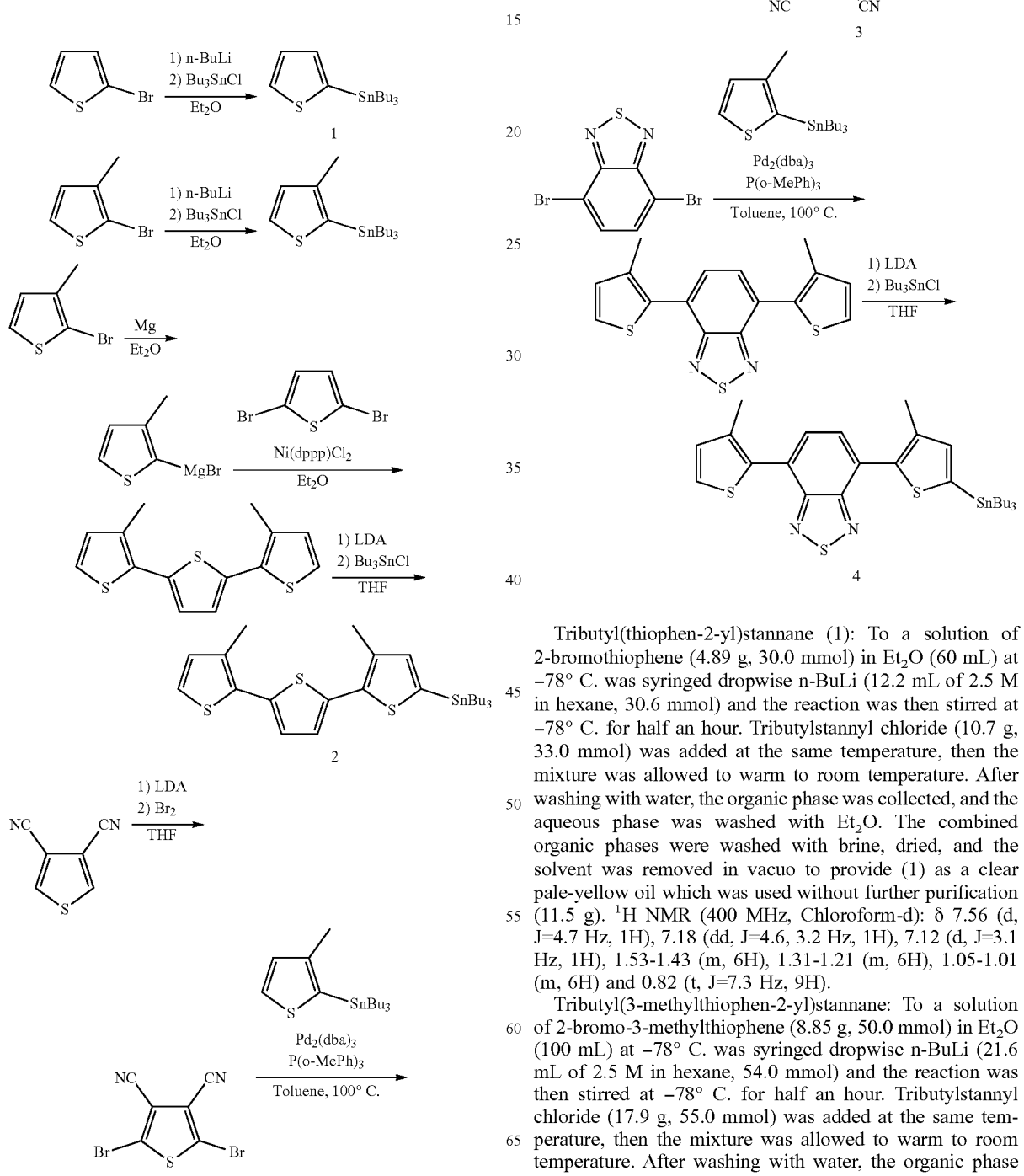

Tributyl(thiophen-2-yl)stannane (1): To a solution of 2-bromothiophene (4.89 g, 30.0 mmol) in Et$_2$O (60 mL) at −78° C. was syringed dropwise n-BuLi (12.2 mL of 2.5 M in hexane, 30.6 mmol) and the reaction was then stirred at −78° C. for half an hour. Tributylstannyl chloride (10.7 g, 33.0 mmol) was added at the same temperature, then the mixture was allowed to warm to room temperature. After washing with water, the organic phase was collected, and the aqueous phase was washed with Et$_2$O. The combined organic phases were washed with brine, dried, and the solvent was removed in vacuo to provide (1) as a clear pale-yellow oil which was used without further purification (11.5 g). $^1$H NMR (400 MHz, Chloroform-d): δ 7.56 (d, J=4.7 Hz, 1H), 7.18 (dd, J=4.6, 3.2 Hz, 1H), 7.12 (d, J=3.1 Hz, 1H), 1.53-1.43 (m, 6H), 1.31-1.21 (m, 6H), 1.05-1.01 (m, 6H) and 0.82 (t, J=7.3 Hz, 9H).

Tributyl(3-methylthiophen-2-yl)stannane: To a solution of 2-bromo-3-methylthiophene (8.85 g, 50.0 mmol) in Et$_2$O (100 mL) at −78° C. was syringed dropwise n-BuLi (21.6 mL of 2.5 M in hexane, 54.0 mmol) and the reaction was then stirred at −78° C. for half an hour. Tributylstannyl chloride (17.9 g, 55.0 mmol) was added at the same temperature, then the mixture was allowed to warm to room temperature. After washing with water, the organic phase was collected, and the aqueous phase was washed with Et₂O. The combined organic phases were washed with brine, dried, and the solvent was removed in vacuo to provide the title compound as a clear pale-yellow oil which was used without further purification (19.6 g). $^1$H NMR (400 MHz, Chloroform-d) δ 7.51 (d, J=4.6 Hz, 1H), 7.05 (d, J=4.5 Hz, 1H), 2.32 (s, 3H), 1.58-1.44 (m, 6H), 1.38-1.26 (m, 6H), 1.15-1.06 (m, 6H), 0.89 (t, J=7.3 Hz, 9H).

3,3"-Dimethyl-2,2':5',2"-terthiophene: A Grignard reagent, prepared by adding Et₂O solution of 2-bromo-3-methylthiophene (2.27 g, 12.8 mmol) into a mixture of Mg shavings (404 mg, 16.6 mmol) and small grain of iodine in 5 mL dry Et₂O, after refluxing for 3 h, and then cooled to room temperature, was slowly added to a solution containing 2,5-dibromothiophene (1.50 g, 6.20 mmol) and Ni(dppp)Cl₂ (3 mol %) in 20 mL dry Et₂O. The reaction mixture was heated to reflux overnight. Upon completion, the reaction was quenched by the addition of 30 mL 1 M HCl, extracted with DCM and washed with H₂O. The organic phase was then dried over MgSO₄ and concentrated under reduced pressure. The crude product was purified via column chromatography (silica gel, hexane), yielding the title compound as a slightly yellow oil, which slowly crystallized (1.60 g, 94%). $^1$H NMR (400 MHz, Chloroform-d) δ 7.15 (d, J=5.1 Hz, 2H), 7.08 (s, 2H), 6.89 (d, J=5.1 Hz, 2H), 2.42 (s, 6H).

Tributyl(3,3"-dimethyl-[2,2':5',2"-terthiophen]-5-yl)stannane (2): To a solution of 3,3"-dimethyl-2,2':5',2"-terthiophene (575 mg, 2.08 mmol) in 20 ml of dry THF, a 2.0 M solution of lithium diisopropylamide (LDA) in hexane (1.20 ml, 2.40 mmol) was added dropwise at 0° C. The mixture was stirred for 1 h at room temperature. Afterwards the solution was cooled to 0° C. again and tri(n-butyl)stannyl chloride (745 g, 2.29 mmol) was added. Finally, the mixture was stirred at room temperature for 1 h. Afterwards the reaction mixture was poured into water and extracted with dichloromethane. The organic phase was washed with brine and the organic phase dried over MgSO₄. The solvent was removed to produce a yellowish oil which was used without further purification (1.25 g). $^1$H NMR (400 MHz, Chloroform-d) δ 7.14 (t, J=5.2 Hz, 1H), 7.09-7.06 (m, 2H), 6.92 (d, J=2.5 Hz, 1H), 6.89 (dd, J=5.1, 2.9 Hz, 1H), 2.43 (s, 3H), 2.42 (s, 3H), 1.62-1.54 (m, 6H), 1.40-1.31 (m, 6H), 1.17-1.05 (m, 6H), 0.91 (t, J=7.3 Hz, 9H).

2,5-Dibromothiophene-3,4-dicarbonitrile: A solution of 3,4-dicyanothiophene (2.41 g, 18.0 mmol) in dry THF (120 mL) under argon, was cooled to −78° C. and 18.9 mL (37.8 mmol) of LDA (2.0 M in solution of THF/n-heptane/ethylbenzene) was added dropwise. After stirring this mixture for 15 min at −78° C., bromine (2.03 mL, 39.6 mmol) was slowly added. The mixture was then stirred for 2 h at −78° C. The reaction was allowed to warm back to room temperature, then quenched by adding 50 mL of a saturated aqueous solution of NH₄Cl. The mixture was extracted with CH₂Cl₂ and the organic layer was dried over magnesium sulfate, filtered and then evaporated to dryness. The crude solid produced was purified by chromatography on silica gel with DCM as eluent to give 2,5-dibromo-3,4-dicyanothiophene as a white solid (3.16 g, 60%).

3,3"-Dimethyl-[2,2':5',2"-terthiophene]-3',4'-dicarbonitrile: A mixture of 2,5-dibromothiophene-3,4-dicarbonitrile (1.04 g, 3.55 mmol), Pd(PPh₃)₄(82.0 mg, 0.071 mmol), and tributyl(3-methylthiophen-2-yl)stannane (3.02 g, 7.81 mmol) was heated to 80° C. in dry DMF (35 mL) under argon for 24 h. After cooling, a saturated solution of NH₄Cl (40 mL) was added and the mixture was extracted with DCM. The collected organic layer was then washed with brine. After drying over MgSO₄, the organic layer filtrate was concentrated under vacuum. Purification by column chromatography on silica gel eluting by DCM afforded a yellow solid (0.96 g, 83%). $^1$H NMR (400 MHz, Chloroform-d) δ 7.46 (d, J=5.1 Hz, 2H), 7.02 (d, J=5.1 Hz, 2H), 2.43 (s, 6H).

3,3"-Dimethyl-5-(tributylstannyl)-[2,2':5',2"-terthiophene]-3',4'-dicarbonitrile (3): To a solution of 3,3"-dimethyl-[2,2':5',2"-terthiophene]-3',4'-dicarbonitrile (538 mg, 1.65 mmol) in 20 ml of dry THF, a 2.0 M solution of lithium diisopropylamide (LDA) in hexane (0.90 ml, 1.82 mmol) was added dropwise at −78° C. The mixture was stirred for 0.5 h at this temperature. Afterwards tri(n-butyl)stannyl chloride (0.54 mL, 1.98 mmol) was added at the same temperature. Finally, the mixture was stirred at room temperature for 1 h. Afterwards the reaction mixture was poured into water and extracted with dichloromethane. The organic phase was washed with brine and the organic phase dried over MgSO₄. The solvent was removed to produce a yellowish oil which was used without further purification (1.05 g). $^1$H NMR (400 MHz, Chloroform-d) δ 7.48-7.42 (m, 1H), 7.04-6.99 (m, 2H), 2.46-2.41 (m, 6H), 1.63-1.53 (m, 6H), 1.40-1.31 (m, 6H), 1.19-1.09 (m, 6H), 0.91 (t, J=7.3 Hz, 9H).

4,7-Bis(3-methylthiophen-2-yl)benzo[c][1,2,5]thiadiazole: Tributyl(3-methylthiophen-2-yl)stannane (1.70 g, 4.40 mmol), 4,7-dibromobenzo[c][1,2,5]thiadiazole (588 mg, 2.00 mmol), Pd₂(dba)₃ (37 mg, 2 mol %) and P(o-tol)₃ (49 mg, 8 mol %) were mixed in a Schlenk tube. After replacing the air with argon, toluene (20 mL) was added via syringe. The mixture was stirred overnight at 100° C. After cooling to room temperature, water was added, and the mixture was extracted with dichloromethane (DCM). The organic layers were combined, washed with brine and dried over magnesium sulfate. The solids were removed by filtration, the solvents were removed under vacuum and the residue was chromatographed on a silica gel column (DCM/hexane=2:3), yielding a yellow solid (645 mg, 98%). $^1$H NMR (400 MHz, Chloroform-d) δ 7.68 (s, 2H), 7.42 (d, J=5.1 Hz, 2H), 7.05 (d, J=5.1 Hz, 2H), 2.36 (s, 6H).

4-(3-Methyl-5-(tributylstannyl)thiophen-2-yl)-7-(3-methylthiophen-2-yl)benzo[c][1,2,5]thiadiazole (4): To a solution of 4,7-bis(3-methylthiophen-2-yl)benzo[c][1,2,5]thiadiazole (1.31 g, 4.00 mmol) in 60 ml of dry THF, a 2.0 M solution of lithium diisopropylamide (LDA) in hexane (2.00 ml, 4.00 mmol) was added dropwise at −78° C. The mixture was stirred for 0.5 h at this temperature. Afterwards tri(n-butyl)stannyl chloride (1.09 mL, 4.00 mmol) was added at the same temperature. Finally, the mixture was allowed to warm back to room temperature and stirred for 1 h. Afterwards the reaction mixture was poured into water and extracted with dichloromethane. The organic phase was washed with brine and the organic phase dried over MgSO₄. The solvent was removed and produced a yellowish oil which was used without further purification (2.51 g). $^1$H NMR (400 MHz, Chloroform-d) δ 7.69-7.63 (m, 2H), 7.44-7.39 (m, 1H), 7.12-7.06 (m, 1H), 7.07-7.01 (m, 1H), 2.40-2.32 (m, 6H), 1.66-1.57 (m, 6H), 1.42-1.33 (m, 6H), 1.18-1.11 (m, 6H), 0.92 (t, J=7.3 Hz, 9H).

Scheme 2: Synthesis of the Conjugated Ligands (Reaction Conditions:

(i) Boc2O, Et3N, DCM, R.T., (ii) NBS, Chloroform, R.T., (iii) Pd2(dba)3, P(o-MePh)3, Toluene, 100° C., (iv) HI, Methanol, R.T.):

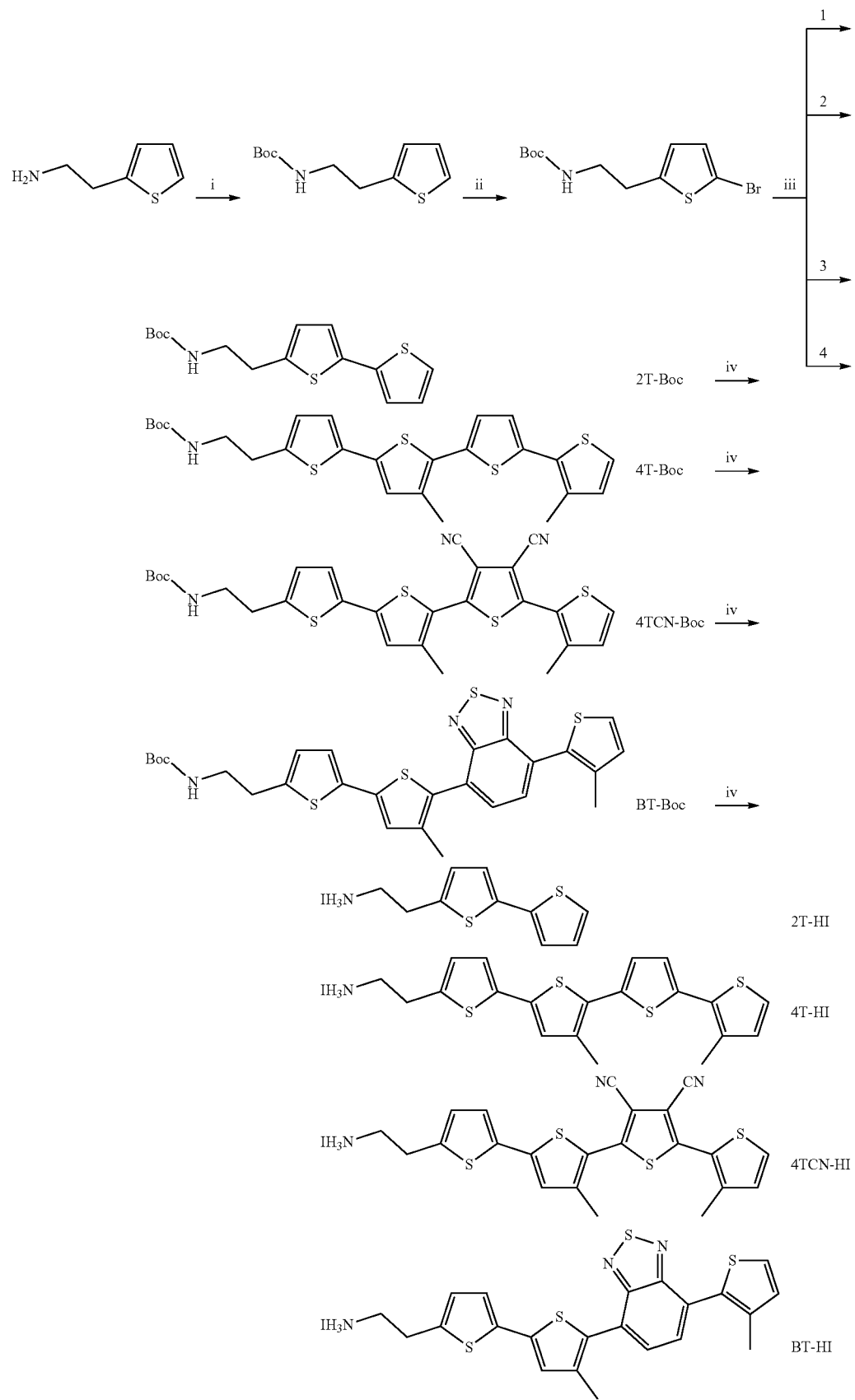

tert-Butyl(2-(thiophen-2-yl)ethyl)carbamate: 2-(Thiophen-2-yl)ethan-1-amine (7.63 g, 60.0 mmol) and 150 mL dry dichloromethane were added to a dried 250-mL Schlenk flask. Then, triethylamine (9.41 g, 93.0 mmol) was added to the solution. Di-tert-butyl dicarbonate (15.71 g, 72.00 mmol) was then added portion-wise which caused bubbles to evolve from the solution. After 4 h, the reaction mixture was placed in a separation funnel and washed with water. The organic layer was collected, dried over magnesium sulfate, and after filtration, the solvent was removed under reduced pressure to provide a yellow oil (98%), which was directly used for the next bromination step without further purification. $^1$H NMR (400 MHz, Chloroform-d) δ 7.17-7.14 (m, 1H), 6.94 (dd, J=5.2, 3.4 Hz, 1H), 6.84-6.82 (m, 1H), 4.65 (s, 1H), 3.40 (d, J=6.5 Hz, 2H), 3.01 (t, J=6.7 Hz, 2H), 1.44 (s, 9H).

tert-Butyl(2-(5-bromothiophen-2-yl)ethyl)carbamate: tert-Butyl(2-(thiophen-2-yl)ethyl)carbamate (3.75 g, 16.5 mmol) was added to a 250-mL flask and dissolved in 50 mL chloroform. The reaction vessel was then wrapped in aluminum foil to exclude light, and NBS (3.08 g, 17.3 mmol) was then added portion wise. After 18 h, the reaction mixture was diluted with chloroform. This mixture was washed with water and then with brine. The organic layer was collected, dried over magnesium sulfate, and concentrated under reduced pressure to provide the crude product as a light-yellow oil. The product was purified by column chromatography with dichloromethane as eluent (90%). $^1$H NMR (400 MHz, Chloroform-d) δ 6.87 (d, J=3.6 Hz, 1H), 6.59 (d, J=3.8 Hz, 1H), 4.64 (s, 1H), 3.35 (d, J=6.5 Hz, 2H), 2.93 (t, J=6.7 Hz, 2H), 1.44 (d, J=2.5 Hz, 9H).

General Method for the Synthesis of Boc Protected Ligands:

tert-Butyl(2-(5-bromothiophen-2-yl)ethyl)carbamate (612 mg, 2 mmol), Pd$_2$(dba)$_3$ (37 mg, 2 mol %), P(o-tol)$_3$ (49 mg, 8 mol %) and the corresponding organotin reagent (2.2 mmol) were mixed in a Schlenk tube. After replacing the air with argon, toluene (20 mL) was added via syringe. The mixture was stirred for 0.5 hours at 100° C. After cooling to room temperature, water was added, and the mixture was extracted with dichloromethane (DCM). The organic layers were combined, washed with brine and dried over magnesium sulfate. The solids were removed by filtration, solvents were removed under vacuum and the residue was chromatographed on a silica gel column as described below. The products were then converted to ammonium salts by adding HI aqueous solution to their methanol solutions.

tert-Butyl(2-([2,2'-bithiophen]-5-yl)ethyl)carbamate (2T-Boc)

The crude product was purified by column chromatography with dichloromethane:hexane (1:1) as the eluent. Colorless liquid (72%). $^1$H NMR (400 MHz, Chloroform-d) δ 7.19-7.17 (m, 1H), 7.10 (dd, J=3.7, 1.4 Hz, 1H), 7.00 (d, J=3.5 Hz, 1H), 6.99 (d, J=3.5 Hz, 1H), 6.73 (d, J=3.7 Hz, 1H), 4.68 (s, 1H), 3.41 (d, J=6.5 Hz, 2H), 2.98 (t, J=6.7 Hz, 2H), 1.45 (s, 9H).

tert-Butyl(2-(3''',4'-dimethyl-[2,2':5',2'':5'',2'''-quaterthiophen]-5-yl)ethyl)carbamate (4T-Boc)

The product was purified with the same method of 2T-Boc. Yellow solid (68%). $^1$H NMR (400 MHz, Chloroform-d) δ 7.15 (d, J=5.1 Hz, 1H), 7.08 (s, 2H), 6.99 (d, J=3.6 Hz, 1H), 6.91 (s, 1H), 6.89 (d, J=5.1 Hz, 1H), 6.73 (d, J=3.6 Hz, 1H), 4.67 (s, 2H), 3.40 (s, 2H), 3.08-2.91 (m, 2H), 2.41 (d, J=10.5 Hz, 6H), 1.45 (s, 9H).

tert-Butyl(2-(3'',4''-dicyano-3''',4'-dimethyl-[2,2':5',2'':5'',2'''-quaterthiophen]-5-yl)ethyl)carbamate (4TCN-Boc)

The product was purified by column chromatography with dichloromethane: ethyl acetate (10:1) as the eluent. Orange solid (70%). $^1$H NMR (400 MHz, Chloroform-d) δ 7.46 (d, J=5.1 Hz, 1H), 7.08 (d, J=3.6 Hz, 1H), 7.02 (d, J=5.1 Hz, 1H), 7.00 (s, 1H), 6.77 (d, J=3.7 Hz, 1H), 4.68 (s, 1H), 3.42 (d, J=7.5 Hz, 2H), 3.01 (t, J=6.8 Hz, 2H), 2.43 (d, J=6.5 Hz, 6H), 1.45 (s, 9H).

tert-Butyl(2-(4'-methyl-5'-(7-(3-methylthiophen-2-yl)benzo[c][1,2,5]thiadiazol-4-yl)-[2,2'-bithiophen]-5-yl)ethyl)carbamate (BT-Boc)

The product was purified by column chromatography with dichloromethane:hexane (2:1) as the eluent. Red solid (82%). $^1$H NMR (400 MHz, Chloroform-d) δ 7.69 (d, J=2.1 Hz, 2H), 7.42 (d, J=5.1 Hz, 1H), 7.09-7.04 (m, 3H), 6.76 (d, J=3.5 Hz, 1H), 4.70 (s, 1H), 3.43 (d, J=6.9 Hz, 2H), 3.01 (t, J=6.6 Hz, 2H), 2.36 (d, J=0.9 Hz, 6H), 1.46 (s, 9H).

General Method for the Synthesis of Ammonium Salt Ligands:

The respective Boc protected ligand (1 mmol) was dissolved in 20 mL methanol (some DCM was added to aid solubility where needed), and aqueous HI solution was then added at 0° C. to cleave the BOC protecting group and in-situ from the ammonium iodides of the ligands. After stirring for 6 h at room temperature, the solvents were removed under vacuum. Diethyl ether was added to the residue, the solid products were collected by filtration, and washed several times with diethyl ether. The products were dried under vacuum for further use.

2T-HI:

white powder (90%). $^1$H NMR (400 MHz, DMSO-d$_6$) δ 7.81 (s, 3H), 7.47 (dd, J=5.3, 1.4 Hz, 1H), 7.23 (dd, J=3.5, 1.3 Hz, 1H), 7.15 (d, J=3.5 Hz, 1H), 7.06 (dd, J=5.1, 3.5 Hz, 1H), 6.92 (d, J=3.6 Hz, 1H), 3.05 (d, J=4.0 Hz, 4H).

4T-HI:

yellow powder (75%). $^1$H NMR (400 MHz, DMSO-d$_6$) δ 7.80 (s, 3H), 7.47 (d, J=5.1 Hz, 1H), 7.26-7.19 (m, 3H), 7.17 (s, 1H), 7.01 (d, J=5.1 Hz, 1H), 6.96 (d, J=3.5 Hz, 1H), 3.09 (q, J=4.6 Hz, 4H), 2.38 (d, J=2.0 Hz, 6H).

4TCN-HI:

orange powder (85%). $^1$H NMR (400 MHz, DMSO-d$_6$) δ 7.84 (d, J=5.1 Hz, 1H), 7.79 (s, 3H), 7.34 (s, 1H), 7.33 (d, J=3.8 Hz, 1H), 7.16 (d, J=5.0 Hz, 1H), 7.02-6.97 (m, 1H), 3.08 (d, J=3.2 Hz, 4H), 2.39 (d, J=1.9 Hz, 6H).

BT-HI:

red powder (83%). $^1$H NMR (500 MHz, DMSO-d$_6$) δ 7.88-7.71 (m, 5H), 7.65 (t, J=4.6 Hz, 1H), 7.27-7.19 (m, 2H), 7.08 (d, J=4.3 Hz, 1H), 6.95 (t, J=3.5 Hz, 1H), 3.07 (d, J=5.7 Hz, 4H), 2.30 (dd, J=17.2, 3.6 Hz, 6H).

2D Perovskite Nanocrystal Growth:

All solution preparations and thin film growth experiments were carried out inside a nitrogen-filled glove box with oxygen and water levels less than 1 ppm. As-synthesized 4T-HI (10.6 mg, 20 μmol) and Pb$_2$ (4.6 mg, 10 μmol) were dissolved in 1 mL of anhydrous dimethyl formamide (DMF) and 1 mL of anhydrous chlorobenzene (CB) inside a 4 mL vial. The solution was then diluted 60 times with an acetonitrile/chlorobenzene (1:2.5 volume ratio) co-solvent. Before use, the diluted solution was further diluted 5 times with either chlorobenzene (CB) or CB/acetonitrile (3:1 volume ratio) co-solvent. Si/SiO$_2$ was used as the substrate for the 2D perovskite growth. Si/SiO$_2$ substrates were cleaned by ultrasonication in isopropanol, acetone, water, and isopropanol again for 5 min; then dried using a nitrogen gun. The substrates were then transferred into the glove box and preheated at 80° C. on a hot plate. 10 µL of the diluted solution was dropped onto the Si/SiO$_2$ surface and dried at 80° C. for 10 min. Thin sheets of (4T)$_2$PbI$_4$ grew spontaneously as the solvent evaporated. All other ligands based 2D perovskite derivatives were synthesized using a similar procedure.

2D Perovskite Thin Film Preparation:

Bare Si/SiO$_2$ wafer or glass slides were used as the substrate for spin coating the 2D perovskite thin film. Substrates were cleaned by ultrasonication in isopropanol, acetone, water, and isopropanol again for 5 min; then dried using a nitrogen gun. The substrates were treated with UV-Ozone for 10 min then transferred into a glove box for further use. As-synthesized 4T-HI (53.0 mg, 100 µmol) and Pb$_2$ (23.0 mg, 50 µmol) were dissolved in 0.25 mL of anhydrous DMF under 70° C. The DMF solution (0.2 M) was let cool to room temperature for spin coating. (4T)$_2$Pb$_4$ thin films were prepared by spin coating the DMF solution at 2000 rpm for 60 s, followed by thermal annealing at 200° C. on a hot plate for 10 min in nitrogen. All other ligands based 2D perovskite thin films were prepared using a similar procedure. (BA)$_2$PbI$_4$ thin films were annealed at 100° C., (2T)$_2$PbI$_4$ thin films at 120° C., (4TCN)$_2$PbI$_4$ thin films at 180° C. For (BT)$_2$FAPb$_2$I$_7$ and (BT)$_2$FA$_2$Pb$_3$I$_{30}$ thin films, the optimized annealing temperature is 150° C. Addition of 5% CsI was required for preparation of thin films from (BT)$_2$FA$_2$Pb$_3$I$_{10}$ DMF solution. (2T)$_2$PbI$_4$ forms the desired perovskite phase immediately after solvent drying. For all other thin films an extra thermal annealing step is required to generate the perovskite phase. This difference may be due to the relative size and bulkiness of the ligands and the intermolecular interactions of these conjugated ligands, therefore requiring more reorganization energy to initiate the crystallization process.

Characterization:

NMR Spectra:

NMR spectra were measured at room temperature using a Bruker AV 400-MHz spectrometer with CDCl$_3$ or d-DMSO as the solvent and tetramethylsilane (TMS) as internal standard. Chemical shifts of $^1$H NMR were reported as values (ppm) relative to TMS.

Cyclic Voltammetry (CV):

Solution CV were measured using a CHI660 electrochemical analyzer with a three-electrode cell at a scan rate of 100 mV/s in anhydrous dichloromethane (DCM) with tetrabutylammonium hexafluorophosphate (Bu$_4$NPF$_6$, 0.1 mol/L) as the supporting electrolyte. A platinum wire with 2 mm diameter, a Pt wire and a Ag/AgCl (standard) were used as working, counter and reference electrodes, respectively.

Ultraviolet Photoelectron Spectroscopy (UPS):

Thin films of the samples were spin-casted onto gold coated SiO$_2$/Si substrates. UPS data were obtained using a Kratos Axis Ultra DLD spectrometer with He I radiation (21.2 eV) at a pass energy (PE) of 5 eV. Samples were clamped on a stainless-steel sample holder bar. No cleaning or heating of samples was done in the XPS chamber prior to analysis.

Optical Microscopy (OM) Measurements:

OM images of the nanocrystals were taken using an Olympus microscope.

Atomic Force Microscopy (AFM):

Thin film and nanocrystal AFM images were recorded in tapping mode using a Bruker MultiMode 8 atomic force microscope.

Single Crystal Growth and Characterization:

Single crystals of (4T)$_2$PbI$_4$ and (BT)$_2$PbI$_4$ were obtained by slow solvent vapor diffusion from a solution in DMF by vapor diffusion of chloroform and chlorobenzene, yielding very thin orange to reddish plates. Small fragments of a plate were transferred to the goniometer head of a Bruker Quest diffractometer with kappa geometry, an I-µ-S microsource X-ray tube, laterally graded multilayer (Goebel) mirror single crystal for monochromatization, a Photon2 CMOS area detector and an Oxford Cryosystems low temperature device. Examination and data collection were performed with Cu K$_\alpha$ radiation ($\lambda$=1.54178 Å) at 150 K. Data were collected, reflections were indexed and processed, and the files scaled and corrected for absorption using APEX3.[5] The space groups were assigned and the structures were solved by direct methods using XPREP within the SHELXTL suite of programs[6,7] and refined by full matrix least squares against F$^2$ with all reflections using Shelxl2018[8] using the graphical interface Shelxle.[9,10] If not specified otherwise H atoms attached to carbon and nitrogen atoms were positioned geometrically and constrained to ride on their parent atoms, with carbon hydrogen bond distances of 0.95 Å for aromatic C—H, 1.00, 0.99 and 0.98 Å for aliphatic C—H, CH$_2$ and CH$_3$ and nitrogen hydrogen distances of 0.91 Å for NH$_3$ moieties, respectively. Methyl and ammonium H atoms were allowed to rotate but not to tip to best fit the experimental electron density. U$_{iso}$(H) values were set to a multiple of U$_{eq}$(C/N) with 1.5 for CH$_3$ and NH$_3$, and 1.2 for C—H and CH$_2$ units, respectively.

Transmission Electron Microscopy (TEM):

TEM characterizations were carried out with a JEOL JEM 2100 Plus thermionic transmission electron microscope operated at 200 kV. All images and diffraction patterns were taken under low dose mode in order to avoid damage from the electron beam.

Out-of-Plane XRD:

Thin film out-of-plane XRD was measured with a Rigaku Smart Lab using a Cu K$\alpha$ source ($\lambda$=1.54056 Å).

Grazing Incidence Wide Angle X-Ray Scattering (GI-WAXS):

GIWAXS spectra were taken at beamline 7.3.3. at the Advanced Light Source (ALS) at Lawrence Berkeley National Lab utilizing an incident wavelength of 10 keV. 2D spectra were recorded with a Pilatus 2M-2D detector and integrated to reduce to 1D with the NIKA GIWAXS software.

UV-Vis-NIR Absorption Spectra:

Solution and thin film absorption spectra were obtained on an Agilent UV-Vis-NIR Cary-5000 spectrometer.

Steady State Photoluminescence (PL) Measurements and Time-Resolved Photoluminescence (TRPL) Measurements:

PL images were taken using an Olympus microscope coupled with an X-CITE 120Q UV lamp. Steady-state photoluminescence and time-resolved photoluminescence measurements were performed by employing a home-built confocal micro-photoluminescence setup. A picosecond pulsed diode laser (Pico-Quant, LDH-P-C-450B) with an excitation wavelength of 447 nm (FWHM=50 ps) and a repetition rate of 40 MHz was used to excite the sample for steady state measurements, which was focused by a 40× (NA=0.6) objective. The PL emission was collected with the same objective, dispersed with a monochromator (Andor Technology) and detected by a TE cooled charge coupled device (Andor Technology). For time resolved PL measurements, the excitation density was ~40 nJ/cm². PL dynamics were measured using a single photon avalanche diode (Pico-Quant, PDM series) and a single photon counting module (Pico-Quant). The time resolution of this setup is ~100 ps.

Transient Absorption (TA) Spectroscopy Measurements:

Transient absorption spectra were measured using a femtosecond pump-probe system with a home-built transient absorption microscope. Laser pulses at 1030 nm with 200 fs duration were generated using a 400 kHz amplified Yb:KGW laser system (PHAROS, Light Conversion Ltd.). The probe beam was a white light continuum beam spanning the 450-800 nm spectral region, created by focusing 5% of the 1030 nm fundamental output onto a YAG crystal (4.0 mm thick). The remainder of the output was used to pump an optical parametric amplifier (OPA, TOPAS-Twins, Light Conversion Ltd.) to generate pump pulses with tunable photon energies for transient absorption experiments. For these measurements, the pump wavelength was 400 nm (20 µW). The pump and probe beams were focused down with a reflective objective (40×, 0.5 NA).

Stability Test:

The stability of prepared 2D perovskite thin films regarding their tolerance towards moisture was investigated by direct immersion under water. $(BA)_2PbI_4$ films were used as a reference for comparison purposes. Video about PL evolution under UV light was recorded and XRD patterns of thin films after immersion were compared with those of pristine films.

Device Fabrication and Measurement:

Fundamental electrical properties regarding vertical and lateral charge carrier transport ability were studied by comparison with $(BA)_2PbI_4$. For vertical transport, we employed a ITO/NiO$_x$/2D PVSK thin film/Spiro-OMeTAD/Au construct as the device structure. The nickel oxide (NiO$_x$) film was prepared as follows. 0.1 M nickel (II) acetate tetrahydrate and 0.1 M ethanolamine were mixed in ethanol and stirred at 70° C. for 3 h. The precursor solution was spin-coated on pre-patterned ITO glass at 2000 r.p.m. for 60 s. Then the substrate was annealed at 250° C. for 30 min. Afterwards, the substrate was transferred to an $N_2$ filled glovebox for further process. After the 2D perovskite thin film deposition, the spiro-OMeTAD hole-transporting material (HTM) solution, comprising 65.3 mM spiro-OMeTAD, 9.1 mM lithium bis-(trifluoromethanesulfonyl)imide, and 93.8 mM 4-tert-butylpyridine in chlorobenzene solvent, was then deposited on the perovskite layer by spin-coating at 4000 rpm for 30 s. Films were dried under vacuum overnight before completing the device fabrication process by thermally evaporating 100 nm of gold on top of the HTM layer. For lateral transport, nanocrystals were directly grown on the wafer with pre-patterned platinum electrodes. A Keithley 2400 source meter was used to measure I-V curves in the dark and under white light irradiation (~30 µW/cm²).

Simulations

Density Functional Theory (DFT) Simulations:

We employed the Vienna Ab initio Simulation Package (VASP, version 5.4.4) for density functional theory calculations. The Perdew-Burke-Ernzerhof (PBE) exchange-correlation functional with a projector augmented-wave (PAW) method was used. The kinetic energy cutoff for the plane wave basis sets was set to 500 eV. A 3×3×1 Gamma centered k-point mesh was used for bulk calculations and slab models with 15 Å vacuum space. A 1×1×1 Gamma centered k-point mesh was used for single molecules separated by at least 12 Å of vacuum from its periodic image. Energy convergence for electronic structure optimization was set to $1×10^{-4}$ eV and geometrical optimization was ended when forces acting on all atoms were below 0.025 eV/A. We probed the electronic structures of $PbI_6$ layers by investigating three monolayer $(BA)_2(MA)_{n-1}Pb_nI_{3n+1}$ (n=1, 2, 3) slab models. We calculated work function values for both slab models and four organic linkers (2T, 4T, 4TCN and BT).

Molecular Dynamics (MD) Simulations:

The MYP model for hybrid perovskites was used as a starting point for the molecular dynamics (MD) simulations of the organic-inorganic perovskite systems. The MYP model consists of the sum of organic-organic, organic-inorganic, and inorganic-inorganic interatomic interactions: the organic-organic interactions are described by a standard AMBER force field, the inorganic-inorganic interactions between Pb and I are described using a Buckingham potential, and the organic-inorganic interactions are described as the sum of Buckingham, electrostatic, and Lennard-Jones (LJ) potentials. Here, the reported MYP LJ parameters were rescaled so that a simulation containing integer charges on the metal, halide, and cation reproduced the cohesive energy density of the unscaled simulation. The scaled inorganic-inorganic Buckingham parameters were then used for simulations of $(BA)_2Pb_4$, $(2T)_2PbI_4$, and $(BT)_2PbI_4$ hybrid perovskites.

The surface cation geometries were optimized using ORCA[13] at the $\omega$B97X-D[14]/def2-TVZP[1]. Density Functional Theory level. Standard GAFF parameters were used for the organic cations, with the cation point charges being fit against the electrostatic DFT potential (wB97X-D/def2-TVZP) of the isolated cation with a +1 charge. Water-water interactions were modelled with the SPC/E water model and water-ion interactions were modelled using Lorentz-Berthelot mixing rules. LAMMPS was used to perform the MD simulations. All simulations used a one fs integration timestep and periodic boundary conditions. Long-range electrostatics were modelled using the particle-particle-particle-mesh (PPPM) algorithm and LJ interactions were truncated at 15 Å. Following the MYP model, 1-4 pairwise LJ interactions were scaled by 0.5 and 1-4 electrostatic interactions were scaled by 0.8333. The initial dehydrated hybrid perovskite geometry was generated by constructing an ideal perovskite monolayer composed of 4×0×4 $A_2BX_4$ unit cells. The 2 nm headspace above and below the perovskite monolayer was filled with non-overlapping water molecules at a density of 1 g/cm³. The headspace volume was chosen to ensure that after equilibration, bulk water density was observable above the surface. The simulation was first relaxed in the NVE ensemble with restrained atomic displacements of 0.01 Å per timestep for 50 ps, followed by a 1 ns NPT simulation with the Nose-Hoover thermostat and barostat. During the NPT equilibration, the barostat was only applied to the dimension normal to the perovskite layer to accommodate the large volume changes associated with water penetration into the perovskite layer. An additional 1ns of NVT dynamics at the average volume from the last 100 ps of the NPT equilibration were run and used for calculating the water density profiles. In calculating the water density profiles, statistics for the top and bottom faces of the perovskite were combined. The reported profiles are averaged over 5 independent trajectories with errors reported as the standard deviation across the trajectories.

Those skilled in the art will recognize that numerous modifications can be made to the specific implementations described above. The implementations should not be limited to the particular limitations described. Other implementations may be possible.

We claim:
1. An organic-inorganic hybrid perovskite of Formula I:

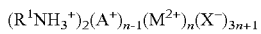

wherein:
($R^1NH_3^+$) represents an asymmetric mono-ammonium cationic moiety:

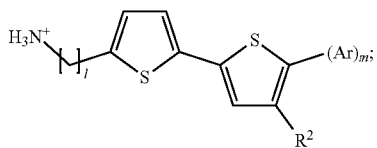

$A^+$ represents a cation $Cs^+$, $Rb^+$, $CH_3NH_3^+$, $CH_3CH_2NH_3^+$, or

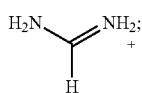

$R^2$ is —H, —F, —Cl, —Br, —I, -Me, -Et, —OMe, —OEt, —SMe, —SEt, —CN, —NO$_2$, —COMe, —CHO, —COOMe, or —NH—COMe;

(Ar)$_m$ represents a conjugated and optionally substituted aryl or hetero aryl system, or a combination thereof, wherein each aryl or hetero aryl ring in the conjugated and optionally substituted aryl or hetero aryl system may be same or different, wherein aryl or hetero aryl may be optionally substituted by —F, —Cl, —Br, —I, -Me, -Et, —OMe, —OEt, —SMe, —SEt, —CN, —NO$_2$, —COMe, —CHO, —COOMe, —NH—COMe, or any combination thereof;

$M^{2+}$ represents a divalent metal cation $Pb^{2+}$, $Sn^{2+}$, $Ge^{2+}$, $Cu^{2+}$, $Zn^{2+}$, $Cd^{2+}$, $Hg^{2+}$, $Ni^{2+}$, $Co^{2+}$, $Fe^{2+}$, $Mn^{2+}$, $Cr^{2+}$, $V^{2+}$, $Pd^{2+}$, $Pt^{2+}$, or a combination thereof; or a combination of one monovalent metal cation selected from the group consisting of $Ag^+$, $Cu^+$, $Tl^+$, $Au^+$, and one trivalent metal cation selected from the group consisting of $Bi^{3+}$, $Sb^{3+}$, $In^{3+}$, $As^{3+}$, $Au^{3+}$, $Y^{3+}$, to make the average valence of the metal cation to be 2+;

X is F, Cl, Br or I;
l is 1-4;
m is 0-5; and
n is 1-6;
wherein the positions of $R^2$ and (Ar)$_m$ on the thiophenyl ring can be exchanged.

2. The organic-inorganic hybrid perovskite of claim 1, wherein $A^+$ is $CH_3NH_3^+$, $CH_3CH_2NH_3^+$, or

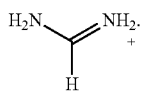

3. The organic-inorganic hybrid perovskite of claim 1, wherein $R^2$ is —F, —Cl, —Br, —I, -Me, -Et, —OMe, —OEt, —SMe, —SEt, —CN, —NO$_2$, —COMe, —CHO, —COOMe, or —NH—COMe.

4. The organic-inorganic hybrid perovskite of claim 1, wherein $R^2$ is -Me.

5. The organic-inorganic hybrid perovskite of claim 1, wherein (Ar)$_m$ represents a conjugated and optionally substituted aryl or hetero aryl system, or a combination thereof, wherein each aryl or hetero aryl ring in the conjugated and optionally substituted aryl or hetero aryl system may be same or different, wherein Ar is selected from the group consisting of:

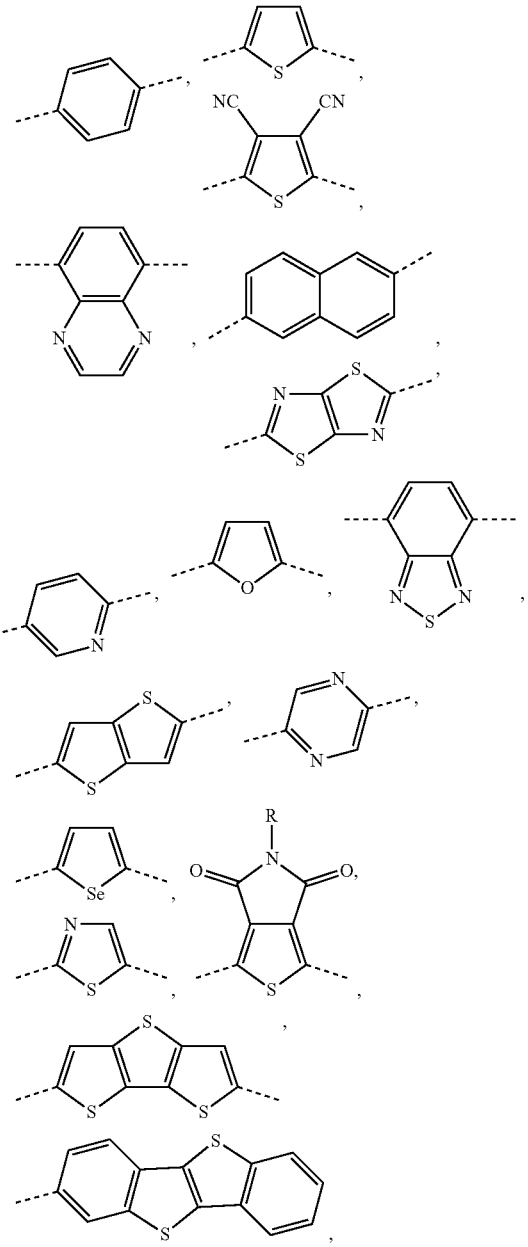

and any combination thereof.

6. The organic-inorganic hybrid perovskite of claim 1, wherein Ar is selected from the group consisting of:

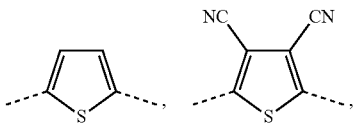

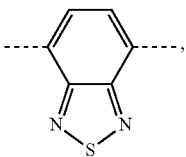

and any combination thereof.

7. The organic-inorganic hybrid perovskite of claim 1, wherein $M^{2+}$ is a divalent metal cation $Pb^{2+}$, $Sn^{2+}$, $Ge^{2+}$, $Cu^{2+}$, $Zn^{2+}$, $Cd^{2+}$, $Hg^{2+}$, $Ni^{2+}$, $Co^{2+}$, $Fe^{2+}$, $Mn^{2+}$, $Cr^{2+}$, $V^{2+}$, $Pd^{2+}$, $Pt^{2+}$, or a combination thereof.

8. The organic-inorganic hybrid perovskite of claim 1, wherein X is Cl, Br or I.

9. The organic-inorganic hybrid perovskite of claim 1, wherein m is 2-4.

10. The organic-inorganic hybrid perovskite of claim 1, wherein ($R^1NH_3^+$) is selected from the group consisting of:

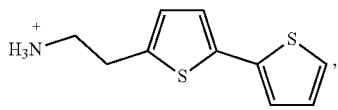

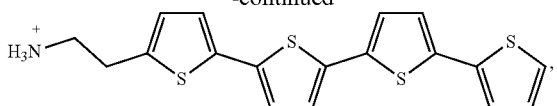

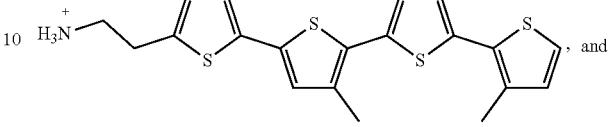

, and

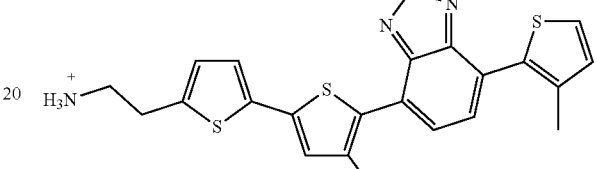

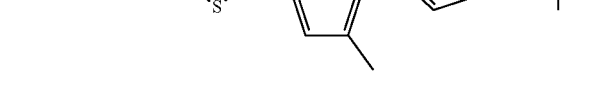.

* * * * *